United States Patent
Tan et al.

(10) Patent No.: US 11,859,245 B2
(45) Date of Patent: Jan. 2, 2024

(54) PRIMER SET AND METHOD FOR DETECTING TELOMERASE ACTIVITY

(71) Applicant: Institute of Zoology, Chinese Academy of Sciences, Beijing (CN)

(72) Inventors: Zheng Tan, Beijing (CN); Kewei Zheng, Beijing (CN); Yuhua Hao, Beijing (CN)

(73) Assignee: INSTITUTE OF ZOOLOGY, CHINESE ACADEMY OF SCIENCES, Beijing (CN)

( * ) Notice: Subject to any disclaimer, the term of this patent is extended or adjusted under 35 U.S.C. 154(b) by 586 days.

(21) Appl. No.: 16/939,098

(22) Filed: Jul. 27, 2020

(65) Prior Publication Data

US 2021/0198716 A1     Jul. 1, 2021

(30) Foreign Application Priority Data

Dec. 25, 2019 (CN) .......................... 201911357551.2

(51) Int. Cl.
| | | |
|---|---|---|
| *C12Q 1/686* | (2018.01) | |
| *C12Q 1/6809* | (2018.01) | |
| *C12Q 1/6853* | (2018.01) | |

(52) U.S. Cl.
CPC ............ *C12Q 1/686* (2013.01); *C12Q 1/6809* (2013.01); *C12Q 1/6853* (2013.01); *C12Q 2521/113* (2013.01); *C12Q 2600/16* (2013.01)

(58) Field of Classification Search
CPC .... C12Q 1/686; C12Q 1/6809; C12Q 1/6853; C12Q 2521/113; C12Q 2600/16; C12Q 1/6876; C12Q 1/6851; C12Q 1/6886
See application file for complete search history.

(56) References Cited

FOREIGN PATENT DOCUMENTS

CN     105648051 A   *   6/2016

OTHER PUBLICATIONS

Szatmari et al., Analytical Biochemistry 282, 80-88, (Year: 2000).*

* cited by examiner

*Primary Examiner* — Cynthia B Wilder
(74) *Attorney, Agent, or Firm* — MATTHIAS SCHOLL P.C.; Matthias Scholl

(57) ABSTRACT

A primer set for detecting telomerase activity, the primer set including a first primer set or a second primer set. The first primer set includes: an upstream primer selected from MTS; and a downstream primer selected from the group consisting of ACX-M4, Beacon ACX62-2C, and Beacon ACX62-10. The second primer set includes: an upstream primer selected from STS or CTS; and a downstream primer selected from the group consisting of ACX, CXT, ACX-M4, Beacon ACX62-2C, or Beacon ACX62-10. The sequences of the primers ACX, CXT, ACX-M4, Beacon ACX62-2C, Beacon ACX62-10, STS, CTS and MTS are shown as SEQ ID NOs: 1 to 8, respectively.

13 Claims, 16 Drawing Sheets

Specification includes a Sequence Listing.

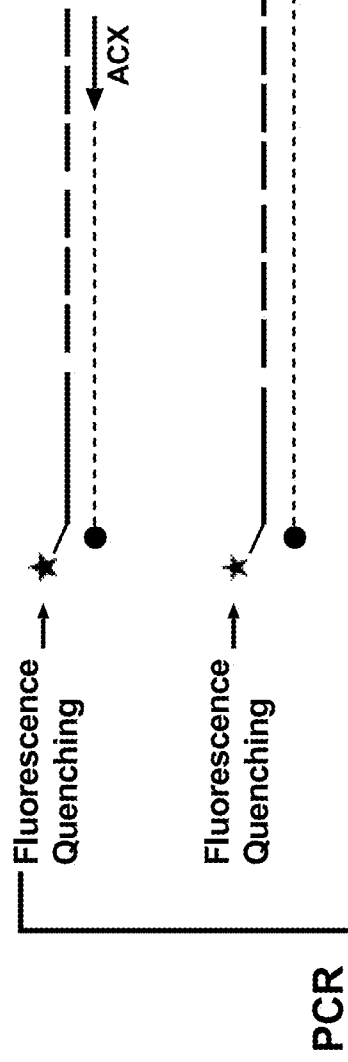
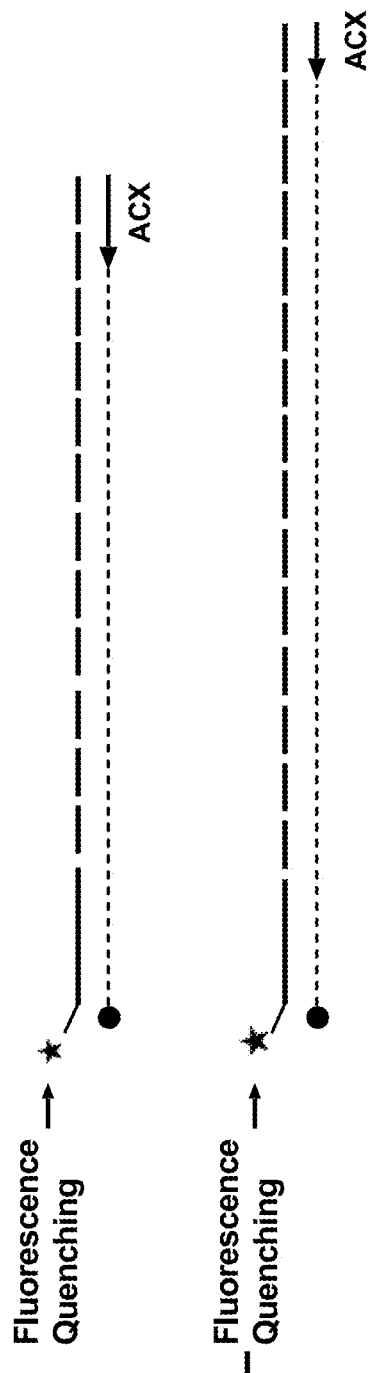

PRIMER SET AND METHOD FOR DETECTING TELOMERASE ACTIVITY

CROSS-REFERENCE TO RELATED APPLICATIONS

Pursuant to 35 U.S.C. § 119 and the Paris Convention Treaty, this application claims foreign priority to Chinese Patent Application No. 201911357551.2 filed Dec. 25, 2019, the contents of which, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, MA 02142.

BACKGROUND

The disclosure relates to the field of telomerase activity assay, and more particularly to a primer set and method for detecting telomerase activity.

Telomerase is a reverse transcriptase capable of adding a six base repeats (GGTTAG) to the end of chromosomes. Telomerase is essential in telomere length maintenance to sustain cell division potential. Known methods of assaying telomerase activity include telomerase elongation method, telomerase repeated amplification protocol (TRAP), quantitative polymerase chain reaction (qPCR), etc.

In the conventional qPCR methods, nucleic acid dyes are used, and a primer dimer tends to form. In addition, the qPCR system fails to detect telomerase activity of single living cells.

SUMMARY

It is an objective of the disclosure to provide a primer set for detecting telomerase activity of a biological sample. In the process of the telomerase activity assay, the primer set of the disclosure does not form a primer dimer.

It is another objective of the disclosure to provide a method for detecting telomerase activity that can detect the telomerase activity of single living cells.

The disclosure provides a primer set for detecting telomerase activity, the primer set comprising a first primer set or a second primer set.

The first primer set comprises:
an upstream primer selected from MTS; and
a downstream primer selected from the group consisting of ACX-M4, Beacon ACX62-2C, and Beacon ACX62-10.

The second primer set comprises:
an upstream primer selected from STS or CTS; and
a downstream primer selected from the group consisting of ACX, CXT, ACX-M4, Beacon ACX62-2C, or Beacon ACX62-10.

The sequences of the primers ACX, CXT, ACX-M4, Beacon ACX62-2C, Beacon ACX62-10, STS, CTS and MTS are shown as SEQ ID NOs: 1 to 8, respectively.

The 5'-end of the upstream primer is labeled with a fluorescent reporter group.

The fluorescent reporter group is located on an iso-dC nucleotide or a dCTP nucleotide at the 5'-end of the upstream primer.

The fluorescent reporter group is selected from the group consisting of FAM (fluorescein amidite), BODIPY (borondipyrromethene), and TAMRA (tetramethylrhodamine).

The disclosure also provides a method for detecting telomerase activity of a biological sample, which is a two-reaction protocol comprising telomerase extension in the presence of the first primer set or the second primer set and qPCR amplification. Specifically, the method comprises:

1) lysing the biological sample with a 3-((3-cholamidopropyl)dimethylammonio)propanesulfonate (CHAPS) lysis buffer to obtain a cell lysate solution;
2) performing a telomerase extension in the cell lysate solution in the presence of the upstream primer of the first primer set or the second primer set of the primer set to obtain a telomerase template; and
3) performing a quantitative PCR amplification with the telomerase template in the presence of a corresponding downstream primer of the upstream primer of the first primer set or the second primer set used in the telomerase extension in 2).

The cell lysate solution in 1) is obtained as follows: suspending cells of the biological sample in a phosphate buffer saline (PBS) solution, centrifuging the PBS solution comprising the cells at 500×g for 3 min, removing a supernatant of the PBS solution and repeating the centrifuging and removing the supernatant for 3 times; resuspending the cells in an isotonic buffer, dispersing the cells, adding the cells to 2 volumes of CHAPS lysis buffer with respect to a volume of the cells, lysing the cells on an ice for 30 min, centrifuging the cells at 16000×g for 20 min, collecting a supernatant and/or storing the supernatant at −80° C.

Optionally, the cell lysate solution in 1) is obtained as follows: adding 1-175 of the CHAPS lysis buffer to a PCR tube, aspirating single or multiple cells of the biological sample into the PCR tube by a flow cytometer or a glass tube under a microscope, and lysing the cells on an ice for 10-30 min to obtain the cell lysate solution.

The method is implemented in a PCR tube provided with 20-4, of a reaction solution comprising 10 μL of 2×PCR mix, 0.8 μL of the upstream primer, 0.8 μL of the downstream primer, 2 μL of the cell lysate solution, and 6.4 μL of double distilled water (ddH$_2$O).

Optionally, the method is implemented in a PCR tube provided with 10 μL of a reaction solution comprising 5 μL of 2×PCR mix, 0.4 μL of the upstream primer, 0.4 μL of the downstream primer, 1 μL of the cell lysate solution, 0.15 μL of dimethylsulfoxide (DMSO), 0.15 μL of 10 mg/mL bovine serum albumin (BSA), and 2.9 μL of ddH$_2$O.

The reaction solution is treated under an extension reaction program and a PCR reaction program consecutively; the extension reaction program comprises incubation at 25° C. for 25 min, and denaturation at 94° C. for 2 min; the PCR reaction program comprises: a) denaturation at 94° C. for 30 s; b) annealing at 57-60° C. for 30 s; c) extension at 72° C. for 30 s; d. repeating operations b)-c) 45-50 times; and e) extension at 72° C. for 10 min.

Optionally, the method is implemented in a PCR tube provided with 10 μL of a first reaction system comprising 5 μL of 2×PCR mix, 0.8 μL of the upstream primer, 2 μL of the cell lysate solution, and 2.2 μL of ddH$_2$O, and 20 μL of a second reaction system comprising 5 μL of 2×PCR mix, 0.8 μL of the downstream primers, 10 μL of telomerase template, and 4.2 μL of ddH$_2$O; and the first reaction system and the second reaction system are added to the PCR tube in two steps.

The PCR tube is treated under an extension reaction program and a PCR reaction program consecutively; the extension reaction program comprises incubation at 25° C. for 10-25 min, and denaturation at 94° C. for 5 min; the PCR reaction program comprises: a) denaturation at 94° C. for 2 min; b) denaturation at 94° C. for 30 s; c) annealing at 57-60° C. for 30 s; d) extension at 72° C. for 30 s; e) repeating operations b)-d) 45-50 times; and f) extension at 72° C. for 10 min.

The CHAPS lysis buffer comprises 15 mM of Tris-HCl (pH 7.5), 2 mM of MgCl$_2$, 1.5 mM of ethylene glycol tetraacetic acid (EGTA), 0.75% of CHAPS (m/v), 15% of glycerol (v/v), 7.5 mM of dithiothreitol (DTT), 0.75 mM of a protease inhibitor 4-(2-aminoethyl)benzenesulfonyl fluoride hydrochloride (AEBSF), 1.5 U/of a RNase inhibitor, and 0.6 mg/mL of BSA.

The following advantages are associated with the primer set and method for detecting telomerase activity of the disclosure: the downstream primer of the first primer set can form a hairpin structure thus preventing the cross-pairing between the two primers to form a primer dimer; the upstream primer sequence of the second primer set is optimized thus preventing the cross-pairing between the two primers to form a primer dimer. Therefore, the primer sets for detecting telomerase activity can prevents the formation of a primer-dimer. The method presents a mix-and-run real-time PCR protocol for quantitating telomerase activity and detects telomerase activity to a single molecule of telomerase.

BRIEF DESCRIPTION OF THE DRAWINGS

FIG. 1A is a schematic diagram illustrating the principle of telomerase extension;

FIG. 1B is a schematic diagram of quenching of fluorescent reporter groups on the complementary strand, when downstream primer extends to the end of the template DNA during quantitative PCR;

FIG. 7A is one of the quantitative PCR amplification curves;

FIG. 7B is a distribution chart of the Ct value of the samples covering the 12 experiments;

DETAILED DESCRIPTION

Figure 2:
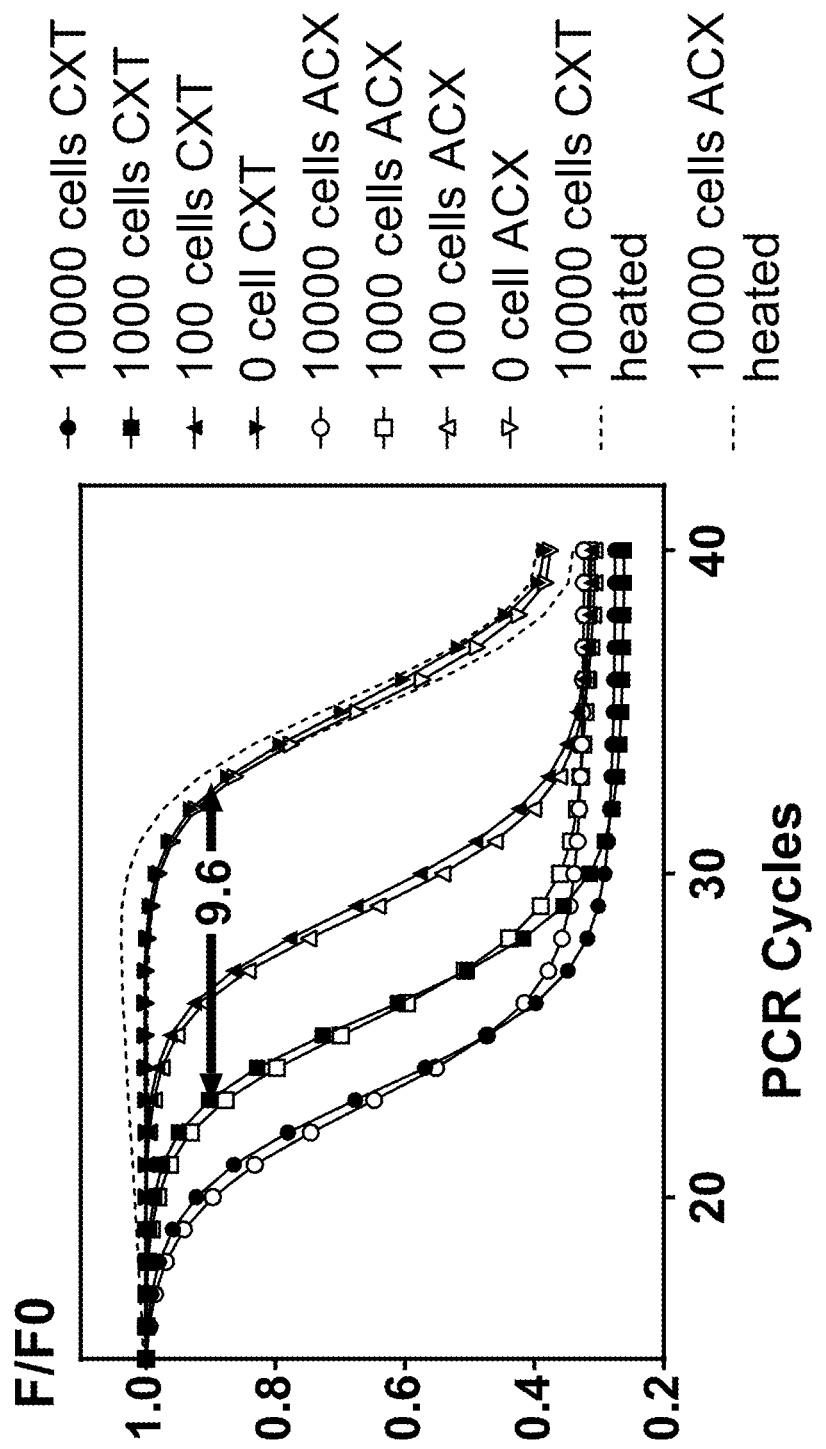
FIG. 2 shows quantitative PCR amplification curves for detecting telomerase activity in 0, 100, 1000, and 10,000 Hela cells, by using primer MTS as an upstream primer, and primers ACX and CXT as downstream primers, respectively.

To further illustrate the disclosure, embodiments detailing a primer set and method for detecting telomerase activity are described below. It should be noted that the following embodiments are intended to describe and not to limit the disclosure.

The disclosure provides a primer set for detecting telomerase activity, comprising a first primer set or a second primer set. The first primer set comprises an upstream primer selected from MTS, and a downstream primer selected from the group consisting of ACX-M4, Beacon ACX62-2C, and Beacon ACX62-10. The second primer set comprises an upstream primer selected from STS or CTS, and a downstream primer selected from the group consisting of ACX, CXT, ACX-M4, Beacon ACX62-2C, or Beacon ACX62-10. The sequences of the primers ACX, CXT, ACX-M4, Beacon ACX62-2C, Beacon ACX62-10, STS, CTS, and MTS are shown as SEQ ID NOs: 1 to 8 in sequence. In the first primer set, the sequence of the downstream primer forms a hairpin structure at low temperature thus avoiding the formation of "primer dimers". The sequence of the upstream primer of the second primer set is also optimized to prevent formation of "cross-paired" of one dimer. Therefore, the primer set for detecting telomerase activity provided by the disclosure effectively prevents primer-dimer formation. The primer sets used in qPCR can measure telomerase activity with sensitivity down to a single telomerase, by which the disclosure offers advantages in linearity, reproducibility and sensibility of detection level over current methods.

Preferably, the upstream primer is labeled with a fluorescent reporter group on a nucleotide, i.e., iso-dC or dCTP at the 5'-end. In the first cycle of PCR, the fluorescent reporter group is quenched by a quenching group on a dCTP nucleotide or an iso-dC nucleotide on a complementary strand. As the PCR reaction proceeds, the fluorescent reporter group labeled on the upstream primer is quenched, leading to a decrease in the total fluorescence signal. Therefore, the changes in the total fluorescence signal can reflect the changes in PCR product yield in real time. The nucleotides iso-dC and iso-dGTP, are unnatural bases that can be recognized by polymerases, while the nucleotides dCTP and dGTP are natural bases.

Preferably, the fluorescent reporter group is selected from the group consisting of FAM (fluorescein amidite), BODIPY (boron-dipyrromethene), and TAMRA (tetramethylrhodamine). BODIPY (boron-dipyrromethene) and TAMRA (tetramethylrhodamine) are cheap and can thus reduce production costs.

The disclosure also provides a method for detecting telomerase activity, which allows for telomerase extension with the first primer set or the second primer set, and qPCR for fluorescent quenching, comprising the steps of:

1) lysing a biological sample with a 3-((3-cholamidopropyl)dimethylammonio)propanesulfonate (CHAPS) lysis buffer to obtain a cell lysate solution;
2) performing a telomerase extension in the cell lysate solution in the presence of the upstream primer of the first primer set or the second primer set to obtain a telomerase template; and
3) conducting a qPCR amplification with the telomerase template in the presence of a corresponding downstream primer of the upstream primer of the first primer set or the second primer set used in telomerase extension.

Preferably, in 1), obtaining the cell lysate solution comprises the steps of:

1) collecting cells of the biological sample; suspending the cells in a phosphate buffer saline (PBS) solution; centrifuging the PBS solution comprising the cells at 500×g for 3 min; removing the supernatant; and repeating the centrifuging and removing the supernatant 3 times;
2) resuspending the cells in an isotonic buffer; dispersing the cells; adding the cells to 2 volumes of CHAPS lysis buffer with respect to a volume of the cells; lysing the cells on an ice for 30 min; centrifuging the cells at 16000×g for 20 min; and collecting a supernatant and/or storing the supernatant at −80° C.; alternatively, adding 1-175 μL of CHAPS lysis buffer to a PCR tube, aspirating single or multiple sample cells into the PCR tube by a flow cytometer or a glass tube under a microscope, and lysing the cells on an ice for 10-30 min to obtain the cell lysate solution.

Preferably, adding the telomerase reaction mix and the qPCR amplification system to a PCR tube in one step. A 20-4, reaction system comprises 10 μL of 2×PCR mix, 0.8 μL of the upstream primer, 0.8 μL of the downstream primer, 2 μL of the cell lysate solution, 6.4 μL of ddH$_2$O. Or a 10-4, reaction system comprises 5 of 2×PCR mix, 0.4 μL of the upstream primer, 0.4 μL of the downstream primer, 1 of the cell lysate solution, 0.15 μL of DMSO, 0.15 μL of 10 mg/mL BSA, and 2.9 of ddH$_2$O. A reaction program comprises an extension reaction program and a PCR reaction program, wherein the extension reaction program: a. incubation at 25° C. for 25 min; b. denaturation at 94° C. for 2 min. The PCR reaction program: a. denaturation at 94° C. for 30 s; b. annealing at 57-60° C. for 30 s; c. extension at 72° C. for 30 s; d. repeating operations b)-c) 45-50 times; e. extension at 72° C. for 10 min.

Preferably, another method to perform the reaction is to add the telomerase extension reaction system and the qPCR amplification system to a PCR tube in two steps. A 10-4, of telomerase extension reaction comprises 5 μL of 2×PCR mix, 0.8 of the upstream primer, 2 μL of the cell lysate solution, and 2.2 μL of ddH$_2$O. A 20-4, of PCR reaction comprises 5 μL of 2×PCR mix, 0.8 μL of the downstream primers, 10 μL of telomerase template, and 4.2 μL of ddH$_2$O. A reaction program comprises an extension reaction program and a PCR reaction program, wherein the extension reaction program: a. incubation at 25° C. for 10-25 min; b. denaturation at 94° C. for 5 min. The PCR reaction program: a. initial denaturation at 94° C. for 2 min; b. denaturation at 94° C. for 30 s; c. annealing at 57-60° C. for 30 s; d. extension at 72° C. for 30 s; e. repeating operations b)-d) 45-50 times; e. extension at 72° C. for 10 min.

Preferably, the CHAPS lysis buffer comprises 15 mM of Tris-HCl (pH 7.5), 2 mM of MgCl$_2$, 1.5 mM of EGTA, 0.75% of CHAPS (m/V), 15% of glycerol (V/V), 7.5 mM of dithiothreitol (DTT), 0.75 mM of protease inhibitor 4-(2-aminoethyl)benzenesulfonyl fluoride hydrochloride (AEBSF), 1.5 U/μL of RNase inhibitor, and 0.6 mg/mL of BSA. The CHAPS lysis buffer of the disclosure does not cause damage to the telomerase in the cells, so that the amplification curve exhibits a good linear relationship. The sequences of the primer set provided by the disclosure are optimized or designed as hairpin structures that are not easy to form primer dimers. Therefore, the method can detect telomerase activity with a single-cell sensitivity level.

The isotonic buffer contains 150 mM NaCl, 1.5 mM MgCl$_2$, 10 mM Tris-HCl (pH 7.5), and 0.5 mM protease inhibitor AEBSF (Sigma-Aldrich). NaCl can be replaced by KCl, and Tris-HCl can be replaced by HEPES-KOH or HEPES-NaOH, and AEBSF can be replaced by phenylmethylsulfonyl fluoride (PMSF).

PCR mix can be plexor qPCR system or GoTaq Probe qPCR Systems from Promega, or can be Luna Universal Probe qPCR Master Mix from NEB, or can be commercial qPCR kits for any other taqman probe methods of other companies. The PCR mix contains dGTP nucleotides and iso-dGTP nucleotides on the fluorescence quenching group. During PCR process, the fluorescent reporter group at the 5'-end of the primer is quenched by quenching groups on the dCTP nucleotide or the iso-dC nucleotide on the complementary strand. Conventionally, the fluorescence quenching group is Dabcyl.

Example 1

Telomerase Extraction:
Collection of Cultured Cells
Cultured Hela cells were dispersed by treatment with trypsin. After an addition of DMEM (dulbecco's modified eagle medium) medium containing 10% fetal bovine serum (FBS), the Hela cells were harvested by centrifugation at 500×g for 20 min and removal of the DMEM medium. The harvested cells were then washed three times with PBS, which comprises the steps of: the cells were resuspended in 20 mL of PBS followed by centrifugation at 500×g for 3 min and removal of the supernatant PBS. The cells were resuspended by addition of 1 mL of PBS and then transferred to a 1 mL Eppendorf tube, followed by centrifugation at 500×g for 3 min and removal of the supernatant PBS. Once again, the cells were resuspended in 1 mL of PBS, followed by centrifugation at 500×g for 3 min and removal of the supernatant PBS.

2. Cell Lysis
The cells obtained in 1) were suspended in 50 μL of isotonic buffer. The cell suspension was added to 100 μL of CHAPS lysis buffer. The cells were pipetted up and down gently to make sure they are fully resuspended. After incubation on ice for 30 min, the cell lysate was centrifuged at 16000×g for 20 min. The supernatant containing active telomerase was collected, and was aliquoted into PCR tubes and could be stored at −70° C. for at least half a year.

Example 2

Detection of telomerase activity: the telomerase activity was detected using a two-reaction protocol comprising telomerase extension and qPCR amplification, where the two reactions were carried out in the same PCR tube. According to the ways of adding the telomerase extension system and the qPCR amplification system to the PCR tube, the method for detecting telomerase activity includes a single-step method and a two-step method. The single-step reaction system means adding the telomerase extension reaction system and the qPCR amplification system to a PCR tube in one step. The two-step reaction system means adding the telomerase extension reaction system and the quantitative PCR amplification system to a PCR tube in two steps.

1. Single-Step Reaction System and Reaction Program Thereof
20 μL-reaction system is shown in Table 1:

TABLE 1

| Composition | Volume (μL) |
| --- | --- |
| 2 × PCR mix | 10 |
| Upstream primer (5 μM) | 0.8 |
| Downstream primer (5 μM) | 0.8 |
| Cell lysate | 2 |
| ddH$_2$O | 6.4 |

The reaction was carried out on a QuantStudio 12K Flex real-time PCR system (Life Technologies, USA) using a PCR program shown in Table. 2.

TABLE 2

| Step | Temperature | Time | Cycles |
| --- | --- | --- | --- |
| 1 | 25° C. | 25 min | 1 |
| 2 | 94° C. | 2 min | 1 |
| 3 | 94° C. | 30 s | 45-50 |
| 4 | 57-60° C. | 30 s | |
| 5 | 72° C. | 30 s | |

Fluorescence signal was measured at the end of each incubation at 72° C.

2. Two-Step Method Reaction System and Reaction Program Thereof.
Reaction system and reaction program thereof were shown in Table 3:

TABLE 3

| | | Composition | Volume (μL) |
| --- | --- | --- | --- |
| Telomerase extension | Reaction system | 2 × PCR mix | 5 |
| | | Upstream primer (5 μM) | 0.8 |
| | | Cell lysate | 2 |
| | | ddH$_2$O | 2.2 |
| | Reaction program | 25° C. 10-25 min | |
| | | 95° C. 5 min | |

TABLE 3-continued

| | | Component | Volume (μL) | |
|---|---|---|---|---|
| qPCR amplification system | Reaction | 2 × PCR mix | 5 | |
| | | Downstream primer (5 μM) | 0.8 | |
| | | Cell lysate | 10 | |
| | | ddH$_2$O | 4.2 | |

| | Step | Temperature | Time | Cycles |
|---|---|---|---|---|
| Reaction program | 1 | 94° C. | 2 min | 1 |
| | 2 | 94° C. | 30 s | |
| | 3 | 57-60° C. | 30 s | 45-50 |
| | 4 | 72° C. | 30 s | |

Fluorescence signal was measured at the end of each incubation at 72° C. Analysis of qPCR amplification result: The starting signal FO was used as an average fluorescence value of per sample after 10-15 cycles of qPCR amplification. The fluorescence value F corresponding to the cycle number of per sample was corrected to F/FO, and the corresponding cycle number was plotted to obtain a PCR amplification curve. The F/FO value of 0.9 or 0.8 was used as a threshold at which the corresponding cycle number on the PCR amplification curve was defined as Ct value.

The two-step method was slightly complicated than the single-step method, but instead separated the telomerase extension reaction and qPCR reaction to reduce primer-dimer formation produced when the telomerase extension reaction is carried out in the presence of the downstream primer and DNA polymerase required for qPCR amplification.

In one embodiment, for detecting telomerase activity, the compositions, which were required for the extension reaction system and the qPCR amplification system, were added to the cell lysate in PCR tube according to the single-step method or the two-step method. That is, extraction of telomerase and detection of telomerase activity were then carried out together in the same PCR tube. The specific steps for preparing the cell lysate in PCR tube comprising: 2 μL of CHAPS lysis buffer was added in the bottom of a PCR tube, and single or multiple sample cells were transferred to the PCR tube through a flow cytometer or a microscopic glass needle, and the cells were lysed on ice for 10-30 min to obtain a cell lysate.

Example 3

Significantly Reduction of Primer Dimer Formation Using Hairpin Primers:

The cell lysate was diluted equivalent to 500 cells in 1 μL CHAPS lysis buffer, and the cell-free CHAPS lysis buffer was used as a telomerase-negative control. Detection of telomerase activity was carried out by the single-step method in Example 2. 2×PCR mix was from the qPCR kit using the Plexor qPCR Systems, the upstream primer was the FAM-(iso-dC) modified primer MTS, and the downstream primers were hairpin primers ACX-M4, Beacon ACX62-2C and Beacon ACX62-10, respectively.

The telomerase extension and the qPCR amplification were carried out on the QuantStudio 12K Flex real-time PCR system in which the annealing temperature in 4) was 60° C.

Analysis of qPCR amplification result: The starting signal FO was used as an average fluorescence value of per sample after 10-15 cycles of qPCR amplification. The fluorescence value F corresponding to the cycle number of per sample was corrected to F/FO, and the corresponding cycle number was plotted to obtain a PCR amplification curve. The F/FO value of 0.9 or 0.8 was used as a threshold at which the corresponding cycle number on the PCR amplification curve was defined as Ct value.

Figure 3:
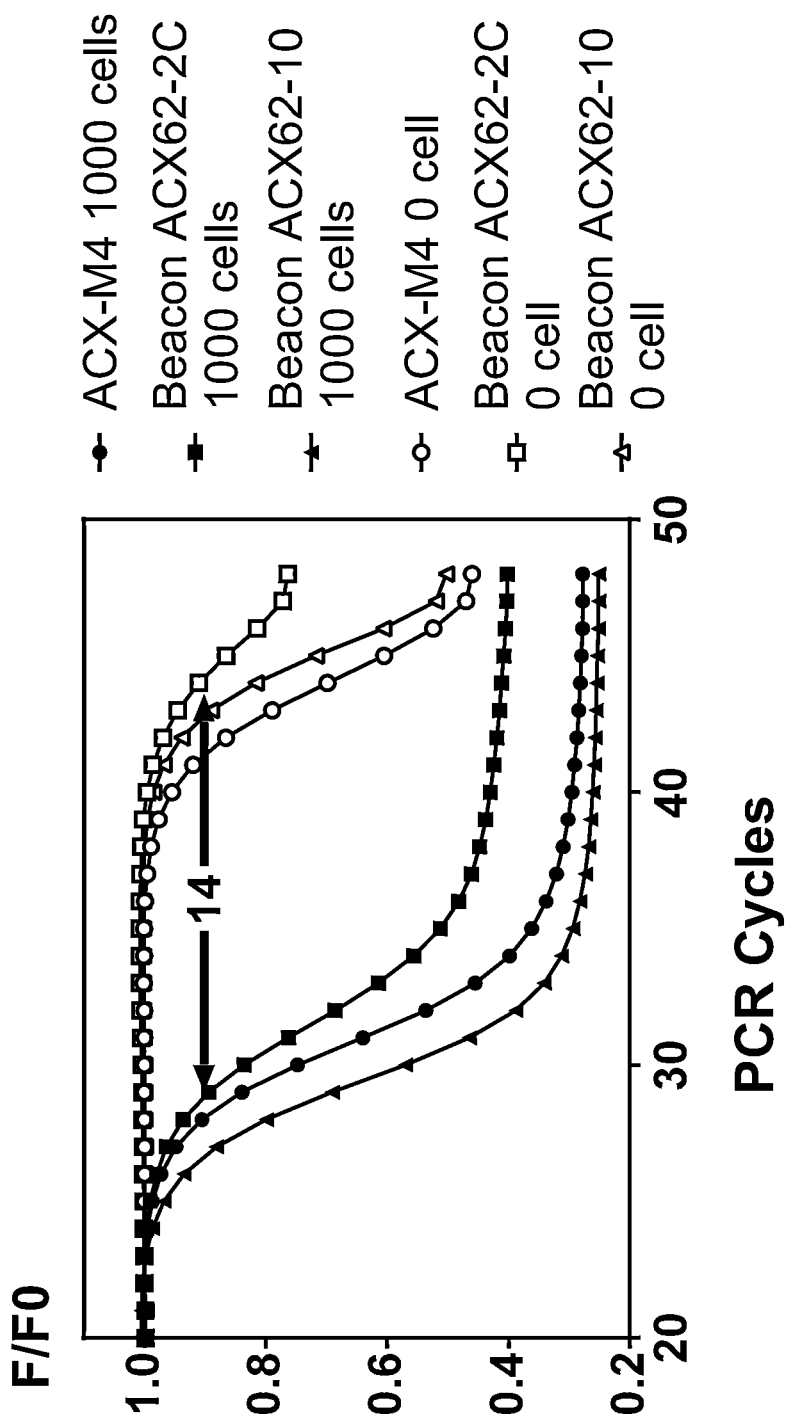
FIG. 3 shows quantitative PCR amplification curves for detecting telomerase activity of 0 and 1000 Hela cells, by using the primer MTS as an upstream primer, and primers ACX-M4, Beacon ACX62-2C, and Beacon ACX62-10 as downstream primers, respectively.

The results of telomerase activity detection were shown in FIG. 3. Analyses revealed that a significantly increased difference occurred between the positive sample and the negative control when the downstream primers is selected from the three hairpin primers, i.e., ACX-M4, Beacon ACX62-2C, and Beacon ACX62-10. When Beacon ACX62-2C was used as the downstream primer, the difference in Ct values, between the positive control of 1000 cells and the negative control of 0 cells or 1000 inactivated cells, expanded to 14, which increased by 4.4 compared with the difference 9.6 in the prior art shown in FIG. 2.

Example 4

Detection of telomerase activity at different concentrations using primers MTS and Beacon ACX62-2C. The cell lysate obtained in Example 1 was diluted with CHAPS lysis buffer to obtain the diluted cell lysates equivalents of 2000, 400, 80, 16, 3.2, and 0.6 Hela cells, respectively. The cell-free CHAPS lysis buffer was used as a telomerase-negative control.

Detection of telomerase activity was carried out by the two-step method in Example 2. 2×PCR mix was from the qPCR kit using Plexor qPCR Systems. The upstream primer was FAM-(iso-dC) modified primer MTS, and the downstream primer was Beacon ACX62-2C. The annealing temperature in 3) of the qPCR reaction program was 60° C.

Figures 4A, 4B:
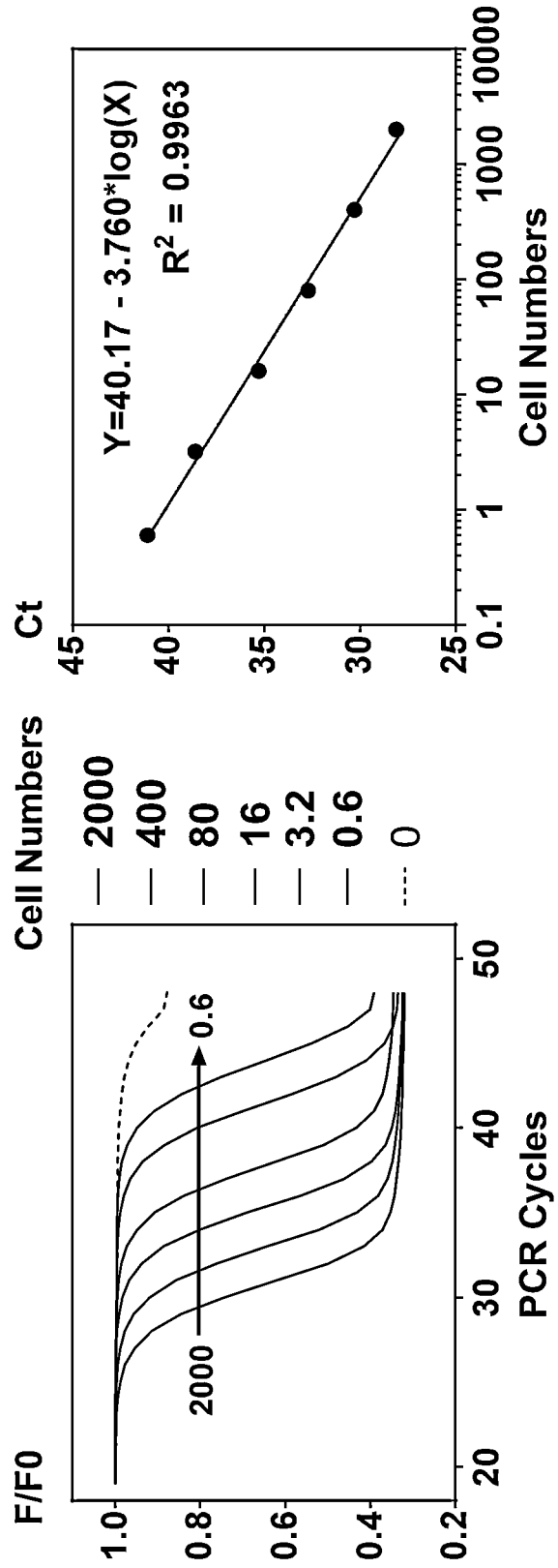
FIG. 4A shows quantitative PCR amplification curves for detecting telomerase activity of 2000, 400, 80, 16, 3.2, and 0.6 Hela cells, by using primer MTS as an upstream primer and primer Beacon ACX62-2C as a downstream primer.
FIG. 4B shows linear relationship between Ct value and logarithm of cell number by quantitative PCR for telomerase activity in 2000, 400, 80, 16, 3.2, and 0.6 Hela cells, by using primer MTS as an upstream primer and primer Beacon ACX62-2C as a downstream primer.

Detection results of telomerase activity in Hela cells were shown in FIGS. 4A and 4B. In FIG. 4A, the abscissa represents number of PCR cycles, the ordinate represents correction value of the fluorescence signal of the sample during each cycle, and the solid lines from left to right represent amplification curves of 20000 cells to 0.6 cells, respectively. The dotted line represents amplification curve of the control sample of 0 cells. In FIG. 4B, a linear relationship between the Ct value and the logarithm of the cell number was obtained by plotting the logarithm of the cell number as the abscissa. Detection of telomerase activity from 0.6 to 20000 cells can be carried out by qPCR amplification, and Ct value and the logarithm of the cell number satisfied certain linear relations. Therefore, Example 4 expands the detection range and is highly sensitive to detect telomerase activity down to single cell with excellent linearity.

Example 5

Reduction of Primer Dimer Formation Using Primer STS:

The cell lysate obtained in Example 1 was diluted with CHAPS lysis buffer to obtain diluted cell lysates equivalents of 20000, 4000, 800, 160, 32, 6.4, 1.3, and 0.2 Hela cells, respectively. The cell-free CHAPS lysis buffer was used as a telomerase-negative control.

Detection of telomerase activity was carried out by the single-step method in Example 2. 2×PCR mix was from the qPCR kit using Plexor qPCR Systems, the upstream primer was FAM-(iso-dC) modified primer STS, and the downstream primer was Beacon ACX62-2C. The annealing temperature in 4) of the qPCR reaction program was 60° C.

Figures 5A, 5B:
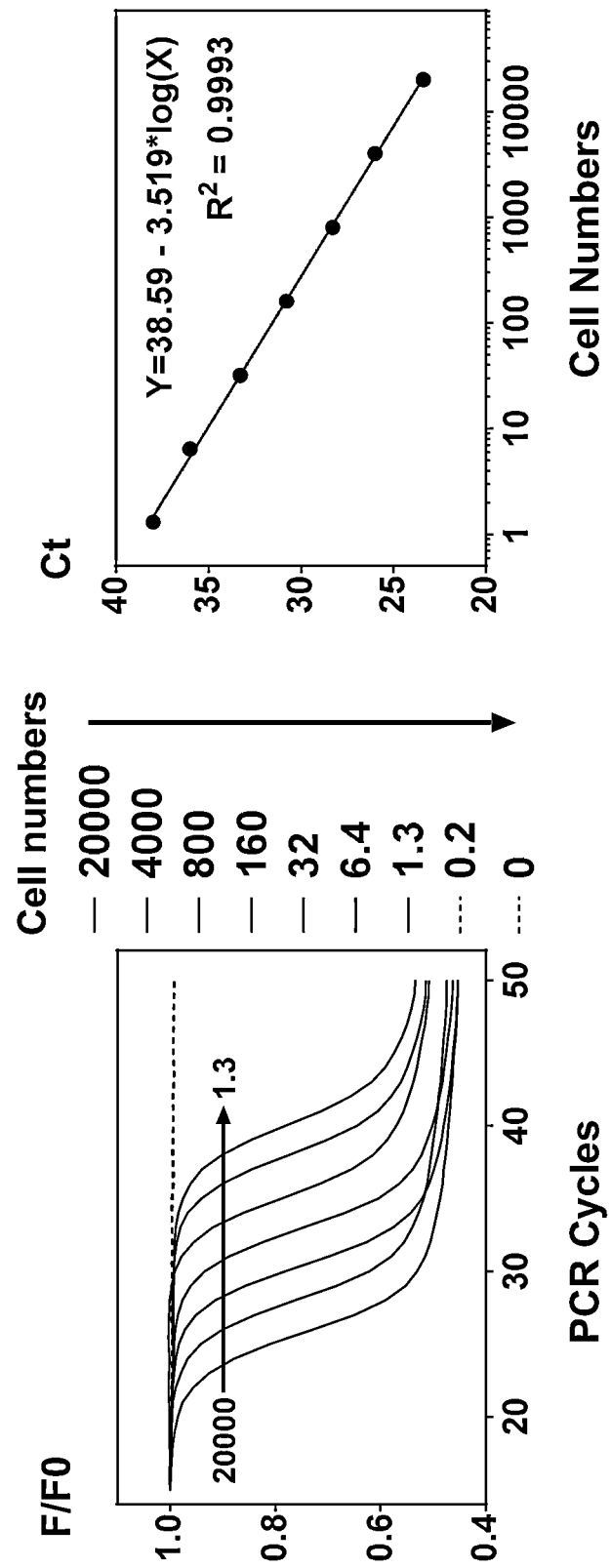
FIG. 5A shows quantitative PCR amplification curves for detecting telomerase activity of 20000, 4000, 800, 160, 32, 6.4, 1.3, and 0.2 Hela cells, by using primer STS as an upstream primer and Beacon ACX62-2C as a downstream primer.
FIG. 5B shows linear relationship between Ct value and logarithm of cell number in quantitative PCR for telomerase activity of 20,000, 4000, 800, 160, 32, 6.4, 1.3, and 0.2 Hela cells, by using primer STS as an upstream primer and primer Beacon ACX62-2C as a downstream primer.

Detection results of telomerase activity in Hela cells were shown in FIGS. 5A and 5B. In FIG. 5A, the abscissa represents number of PCR cycles, the ordinate represents correction value of the fluorescence signal of the sample during each cycle, and the solid lines from left to right represent amplification curves of 20000 cells to 1.3 cells, respectively. The dotted line represents amplification curves of the control sample of 0.2 and 0 cells. In FIG. 5B, a linear relationship between the Ct value and the logarithm of the cell number was obtained by plotting the logarithm of the cell number as the abscissa. Detection of telomerase activity from 1.3 to 20000 cells can be carried out by qPCR amplification, and Ct value and the logarithm of the cell number satisfied certain linear relations. And more particularly, no changes found in the amplification curve of the negative control in 50 cycles of PCR amplification, indicating that the primer STS effectively reduced the primer dimer formation and expanded the detection range of telomerase activity.

Example 6

Detection of Telomerase Activity Using Primers STS and ACX:

Hela cells cultured to 70-80% confluence were detached by treatment with 0.5% trypsin. After an addition of DMEM medium containing 10% fetal bovine serum the Hela cells were harvested by centrifugation at 500×g for 3 min and removal of the DMEM medium. The cells were resuspended in 1 mL of PBS and stained by addition of 1 µg/mL of propidium iodide (PI). The live cells were sorted on a MoFlo XDP high-speed multicolor flow cytometer. 175 µL of CHAPS lysis buffer was added in the bottom of a 1.5 mL EP tube, and by a flow cytometry using single-cell mode, 10,000 cells were aspirated and transferred to the EP tube until final volume reached up to 200 µL. The cells were lysed on ice for 30 min to obtain a cell lysate equivalents of 50 cells/µL.

The cell lysate equivalents of 50 cells/µL was diluted with CHAPS lysate to obtain the diluted cell lysates equivalents of 50, 12.5, 3.2, 0.8 and 0.2 Hela cells, respectively. The cell-free CHAPS lysis buffer was used as a telomerase-negative control.

Detection of telomerase activity was carried out by the one-step method in Example 2. The telomerase extension and qPCR amplification were carried out in a 96-well plate. 2×PCR mix was from the qPCR kit using Plexor qPCR Systems. The upstream primer was FAM-(iso-dC) modified primer STS, and the downstream primer was primer ACX. The annealing temperature in 4) of the qPCR reaction program was 57° C.

Figures 6A, 6B:
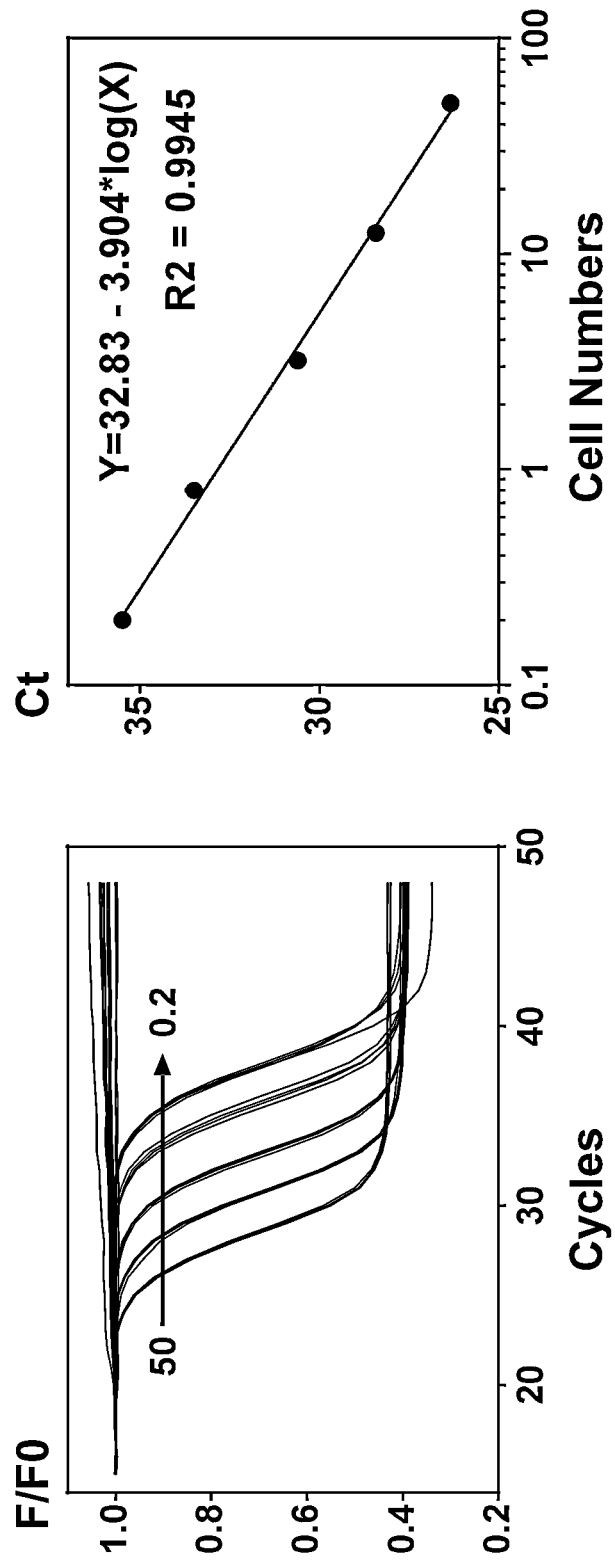
FIG. 6A shows quantitative PCR amplification curves for detecting telomerase activity in 50, 12.5, 3.2, 0.8, and 0.2 Hela cells, by using primer STS modified by FAM-(iso-dC) as an upstream primer, and the primer ACX as a downstream primer.
FIG. 6B shows linear relationship between Ct value and logarithm of cell number in quantitative PCR for detecting telomerase activity in 50, 12.5, 3.2, 0.8, and 0.2 Hela cells, by using primer STS modified by FAM-(iso-dC) as an upstream primer and primer ACX as a downstream primer.

Detection results of telomerase activity in Hela cells were shown in FIGS. 6A and 6B. In FIG. 6A, the abscissa represents number of PCR cycles, the ordinate represents correction value of the fluorescence signal of the sample in each cycle, and the solid lines from left to right represent amplification curves of 50 cells to 0.2 cells, respectively. The dotted line represents amplification curve of the control sample of 0 cells. In FIG. 6B, a linear relationship between the Ct value and the logarithm of the cell number was obtained by plotting the logarithm of the cell number as the abscissa. Detection of telomerase activity from 0.2 to 50 cells can be carried out by qPCR amplification, and Ct value and the logarithm of the cell number satisfied a good linear relation. And more particularly, no amplification signals detected in the negative control in 48 cycles of PCR amplification, indicating that Example 6 is highly sensitive to detect telomerase activity down to single cell with excellent linearity.

Example 7

Repeatability of Method for Detecting Telomerase Activity:

The cell lysate equivalents of 50 cells/µL was obtained by the method in Example 6.

The cell lysate equivalents of 50 cells/µL was diluted with CHAPS lysis buffer to obtain the diluted cell lysates equivalents of 5 and 0.5 HeLa cells/µL. The cell-free CHAPS lysis buffer was used as a telomerase-negative control. Each of the three cell lysates (5, 0.5, 0 HeLa cells/µL) was aliquoted into 20 PCR tubes and stored at −80° C.

Detection of telomerase activity of the three cell lysates was carried out at different times within three months by the single-step method in Example 2. That is, 2 µL of the cell lysate was added to the reaction system, and the telomerase extension and qPCR amplification were carried out in a 96-well plate. 2×PCR mix was from the qPCR kit using Plexor qPCR Systems. The upstream primer was FAM-(iso-dC) modified primer STS, and the downstream primer was ACX. The annealing temperature in 4) of the qPCR reaction program was 57° C.

In the storage period of three months, 12 batches of detections were performed at weekly intervals using the three cell lysates in the Example. The results were shown in FIGS. 7A and 7B. Analysis of qPCR amplification result: The starting signal FO was used as an average fluorescence value of per sample after 10-15 cycles of qPCR amplification. The fluorescence value F corresponding to the cycle number of per sample was corrected to F/FO, and the corresponding cycle number was plotted to obtain a PCR amplification curve. The F/FO value of 0.9 or 0.8 was used as a threshold at which the corresponding cycle number on the PCR amplification curve was defined as Ct value.

Figure 7B:
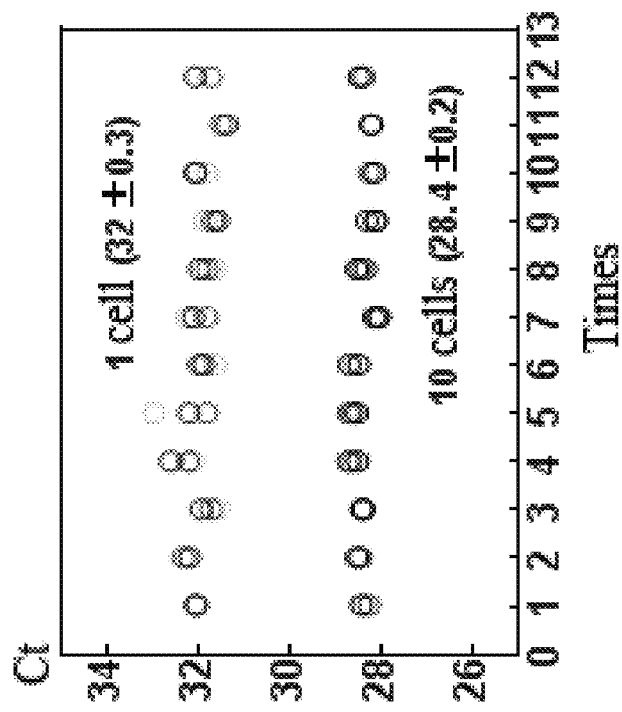
FIG. 7B shows Ct value distribution of telomerase activity in 10, 1, and 0 Hela cells, by using FAM-(iso-dC) modified primer STS as an upstream primer, and primer ACX as a downstream primer. The experiment is repeated 12 times within three months.
Figure 7A:
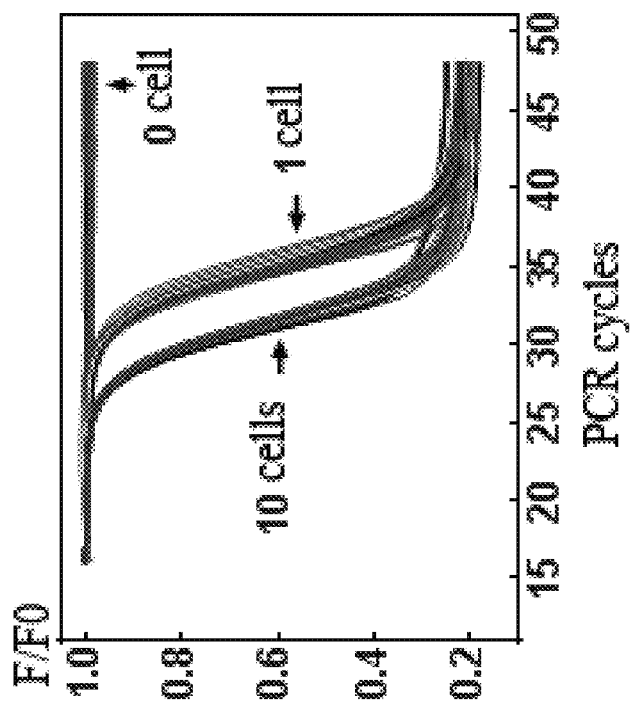
FIG. 7A shows quantitative PCR amplification curves for detecting telomerase activity in 10, 1, 0 Hela cells, by using FAM-(iso-dC) modified primer STS as an upstream primer, and primer ACX as a downstream primer. The experiment is repeated 12 times within three months.

FIG. 7A shows quantitative PCR amplification curves for detecting telomerase activity in 10, 1, 0 Hela cells, respectively. FIG. 7B shows Ct value distribution of telomerase activity in 10, 1, and 0 Hela cells in 12 batches of detections. The results showed the measurements resulted in a very small variation at the Ct values, indicating that telomerase activity can be reliably measured for long-term storage samples.

Example 8

Detection of Telomerase Activity with Sensitivity Down to a Single Telomerase Using Primers STS and ACX:

The cell lysate equivalents of 50 cells/µL was obtained by the method in Example 6.

The cell lysate equivalents of 50 cells/µL was diluted to one and two single cells in 384 µL of CHAPS lysate buffer, respectively. The two diluted cell lysates were both further aliquoted into a 384-well PCR plate for 1 µL per well. 9 µL of reaction solution comprising the telomerase extension system and the qPCR reaction system was then added to each well, 9 µL of reaction solution containing the following compositions: 5 µL of 2×PCR mix (Plexor qPCR Systems), 0.4 µL of FAM-(iso-dC) modified Primer STS (5 µM) (upstream primer), 0.4 µL of primer ACX (5 µM) (downstream primer), 0.15 µL of DMSO, 0.15 µL of 10 mg/mL BSA and 2.9 µL of ddH$_2$O. The above operations were conducted three times for each group of cell lysates.

The cell lysate of 50 cells/µL was diluted with CHAPS lysate buffer to obtain the diluted cell lysates equivalents of 12.5, 3.2, 0.8 and 0.2 Hela cells/µL. 1 µL of the diluted cell lysates were respectively added to a 384-well PCR plate. 9 µL of reaction solution comprising the telomerase extension system and the qPCR reaction system was then added to each well. 9-4, of reaction solution containing the following compositions: 5 µL of 2×PCR mix (from the quantitative PCR kit using Plexor qPCR Systems), 0.4 µL of FAM-(iso-dC) modified primer STS (5 µM) (upstream primer), 0.4 µL of primer ACX (5 µM) (downstream primer), 0.15 µL of DMSO, 0.15 µL of 10 mg/mL BSA and 2.9 µL of ddH$_2$O.

Detection of telomerase activity was carried out by the single-step method in Example 2. Telomerase extension and qPCR amplification were performed on the QuantStudio 12K Flex real-time PCR system in which the annealing temperature in 4) of the PCR reaction program was 60° C.

Figure 8A:
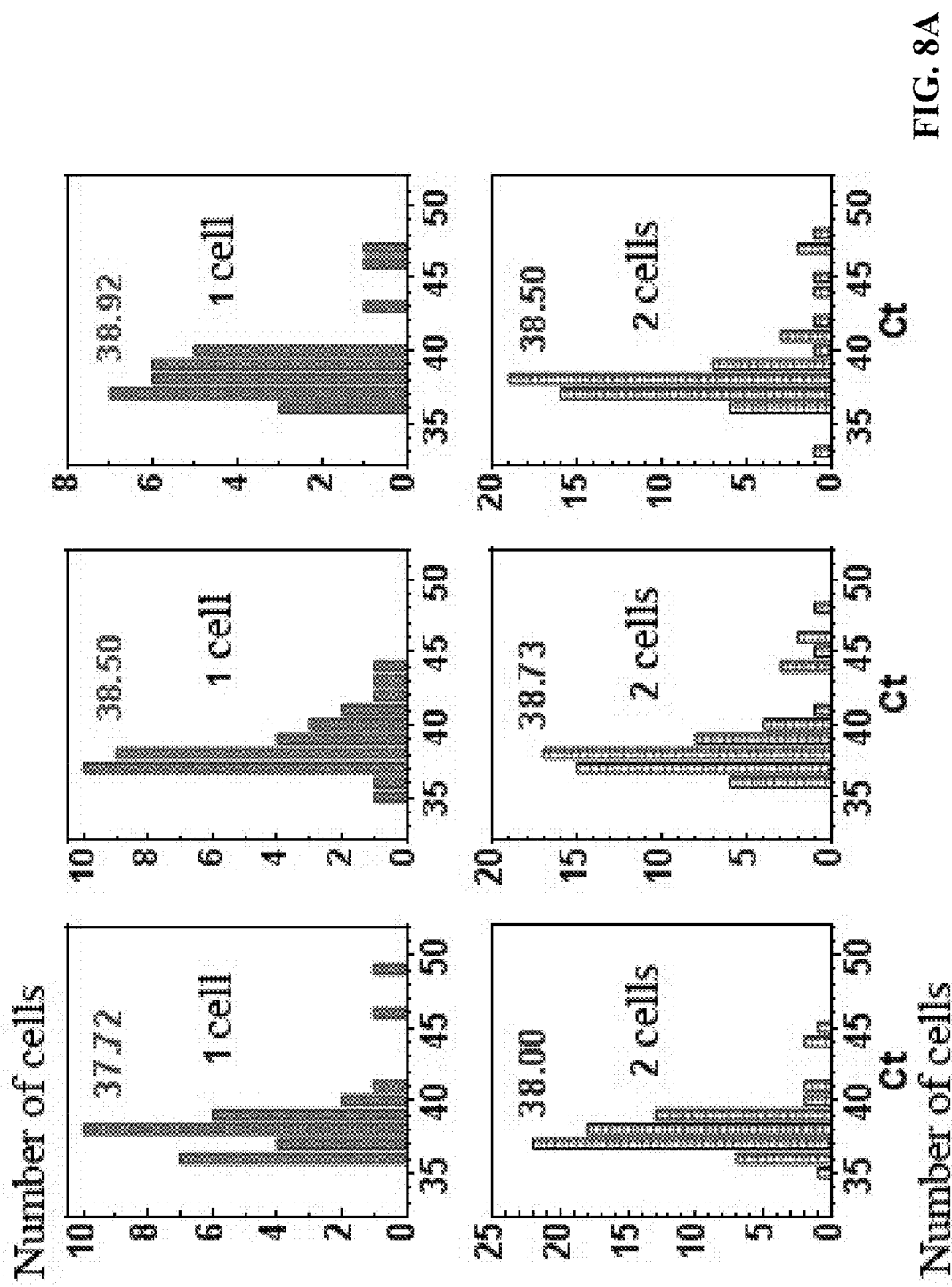
FIG. 8A is a Ct value distribution of telomerase positive samples after one and two Hela cells are diluted to 384 µL and aliquoted into 384 samples. FAM-(iso-dC) modified primer STS is used as an upstream primer, and primer ACX is used as the downstream primer. Each group of samples was subjected to three treatments.
Figures 8B, 8C:
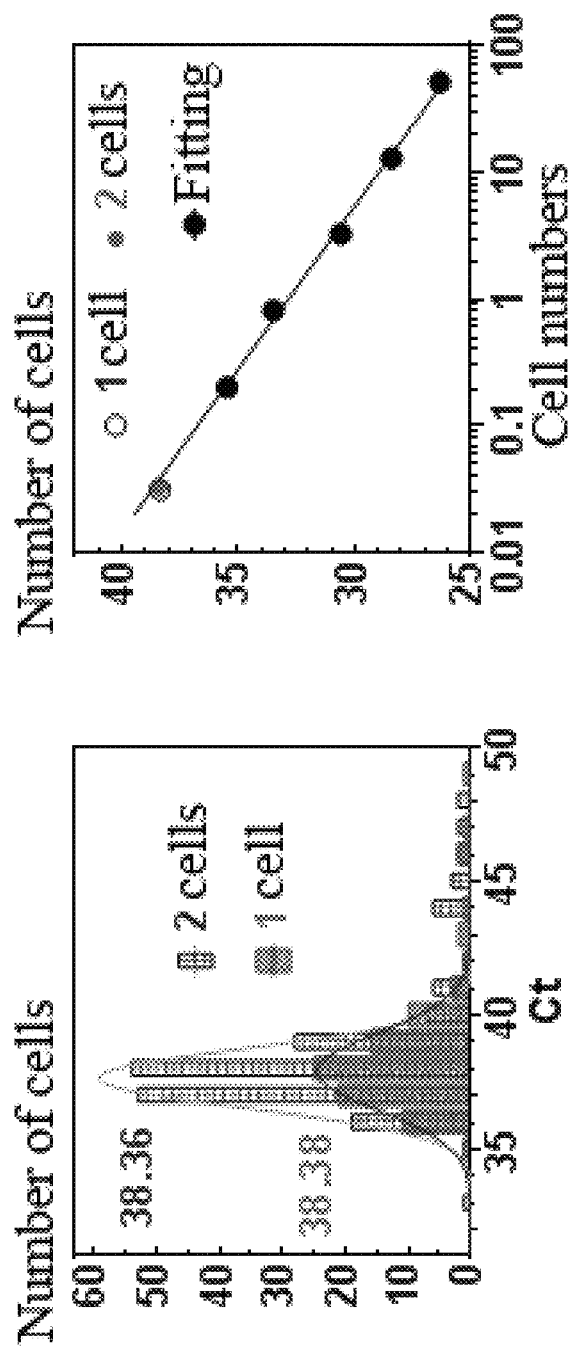
FIG. 8B is a Ct value distribution of a single telomerase obtained by merging and calculating two sets of telomerase positive samples in FIG. 8A.
FIG. 8C is a linear relationship between Ct value and logarithm of cell number obtained by plotting the logarithm of the cell number as an abscissa. Telomerase activities in 50, 12.5, 3.2, 0.8, 0.2 and 1 telomerase test cell(s) are detected by using FAM-(iso-dC) modified primer STS as an upstream primer, and primer ACX as a downstream primer.

FIG. 8A was a Ct value of over diluted Hela cell lysate. Two cell lysate samples equivalent to one and two Hela cells, respectively, were each diluted to a-384-well PCR plate and telomerase activity in each well was measured in triplicate. Primer STS modified with FAM-(iso-dC) was used as an upstream primer, and primer ACX was used as a downstream primer for detecting telomerase activity. FIG. 8B was a Ct value distribution of a single telomerase after merging and calculating two cell lysate samples in FIG. 8A. The results showed that the number of telomerase-positive wells was far smaller than the total number of wells in the plate. The number of telomerase activity in positive cell lysates equivalent of 2 cells/µL was 2 times greater than that of positive cell lysates equivalent of 1 cell/µL. The positive cell lysates feature a wide variation in the telomerase activities around an average of 31.8 Ct, with an average of 32 or 30.8 telomerase molecules per cell.

Detection of Telomerase activity in cell lysates diluted to equivalent of 50, 12.5, 3.2, 0.8, and 0.2 cell/µL. FIG. 8C showed the linear relationship between the Ct value and the logarithm of the cell number fitting as the abscissa. Based on the Ct value of a single telomerase and the average number of telomerases in each cell in FIG. 8B, the Ct value and the number of cells (1/32, 1/30.8) corresponding to a single telomerase molecule were calculated. A linear relationship between the Ct value and the logarithm of the number of cells was shown in FIG. 8C in which the coordinate points of a single telomerase molecule existed on a standard curve. Therefore, the method of the example of the disclosure can be used to detect telomerase activity with sensitivity down to a single telomerase.

Example 9

Anti-Interference Ability of the Method to Detect Telomerase Activity:

According to Example 1, HeLa cells were diluted to equivalent of one cell in 1 µL of CHAPS lysis buffer, and WI-38 cells were diluted to equivalent of 8000, 2000, 500, and 125 cells in 1 µL of CHAPS lysis buffer, respectively. WI-38 cell lysates (8000, 2000, 500, and 125 cells/µL) and HeLa cell lysate equivalent of 1 cells/µL were aliquoted into a 96-well PCR plate for 1 µL per well, followed by the addition of 1 µL of CHAPS lysis buffer per well. The mixture containing 1 µL of one of the four WI-38 cell lysates and 1 µL of the HeLa cell lysates was aliquoted into the 96-well PCR plate for 1 µL per well. The telomerase extension system and qPCR reaction system were prepared according to the method of Example 2. 2×PCR mix was from the qPCR kit using Plexor qPCR Systems. FAM-(iso-dC) modified primer STS was used as the upstream primer, and primer ACX was used as the downstream primer. The annealing temperature in 4) of the qPCR reaction program was 57° C.

WI-38 cells, a normal human cell line composed of fibroblasts derived from lung tissue, had extremely low telomerase activity.

Figures 9A, 9B, 9C:
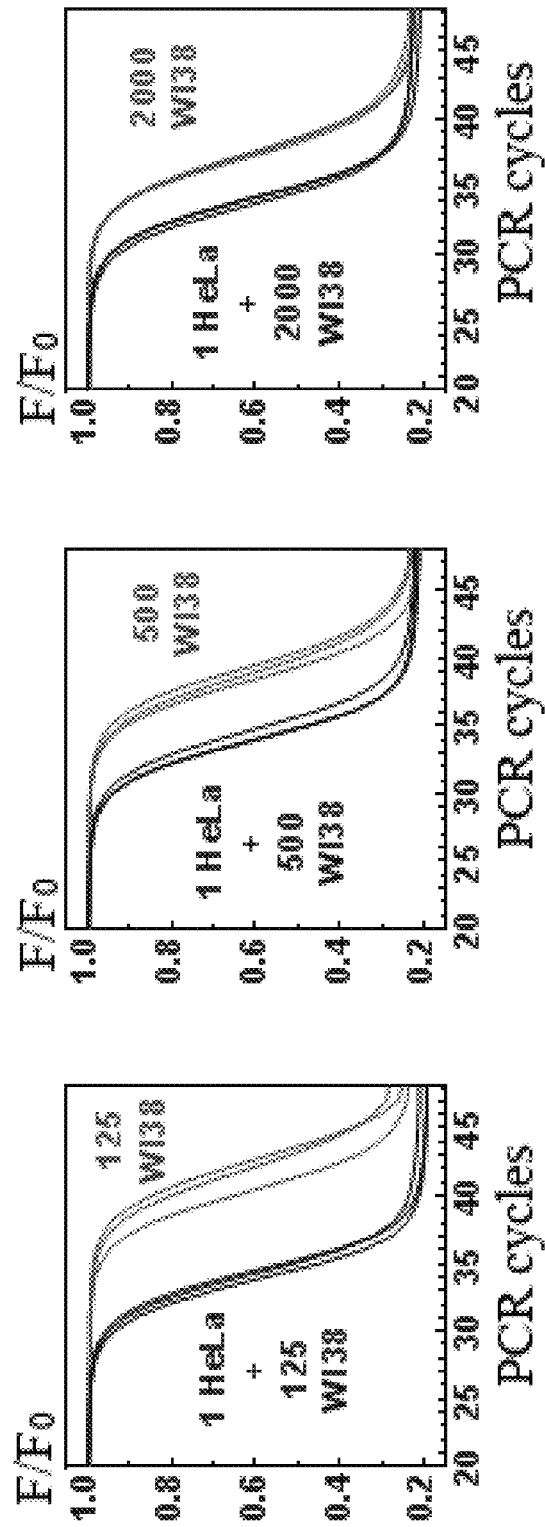
FIG. 9A shows quantitative PCR amplification curves for detecting telomerase activity in a lysate solution comprising 125 WI-38 cells and a lysate solution comprising 1 HeLa cell and 125 WI-38 cells. FAM-(iso-dC) modified primer STS is an upstream primer, and primer ACX is a downstream primer.
FIG. 9B shows quantitative PCR amplification curves for detecting telomerase activity in a lysate solution comprising 500 WI-38 cells and a lysate solution comprising HeLa cell and 500 WI-38 cells. FAM-(iso-dC) modified primer STS is an upstream primer, and primer ACX is a downstream primer.
FIG. 9C shows quantitative PCR amplification curves for detecting telomerase activity in a lysate solution comprising 2000 WI-38 cells and a lysate solution comprising 1 HeLa cell and 2000 WI-38 cells. FAM-(iso-dC) modified primer STS is an upstream primer, and primer ACX is a downstream primer.
Figure 9F:
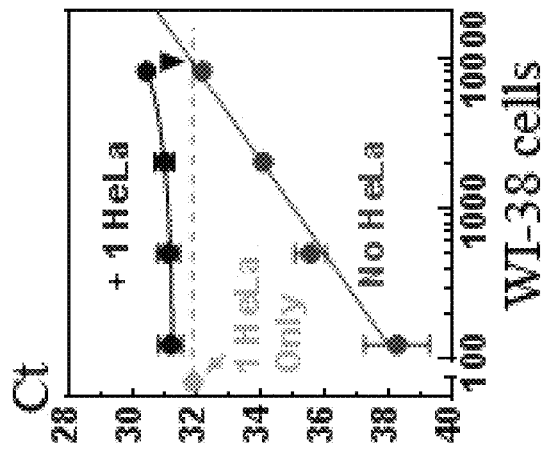
FIG. 9F is a linear relationship between Ct value and logarithm of cell number in quantitative PCR for telomerase activity in FIGS. 9A-9D.
Figure 9E:
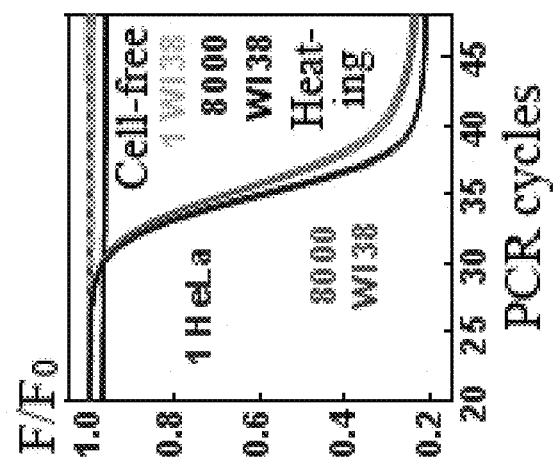
FIG. 9E shows quantitative PCR amplification curves for detecting telomerase activity in a lysate solution comprising 8,000 WI-38 cells and a lysate solution comprising 1 HeLa cell. FAM-(iso-dC) modified primer STS is an upstream primer, and primer ACX is a downstream primer.
Figure 9D:
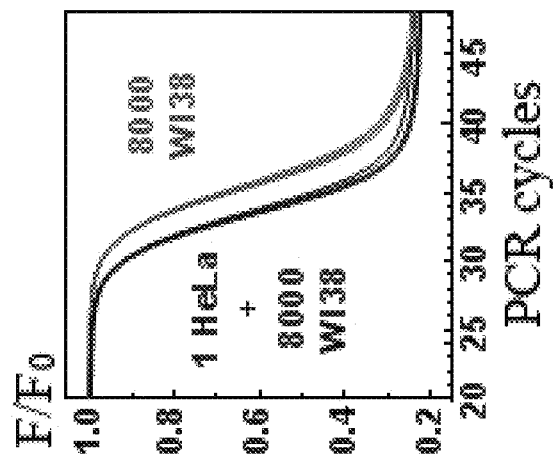
FIG. 9D shows quantitative PCR amplification curves of telomerase activity in a lysate solution comprising 8,000 WI-38 cells and a lysate solution comprising 1 HeLa cell and 8000 WI-38 cells. FAM-(iso-dC) modified primer STS is an upstream primer, and primer ACX is a downstream primer.

FIGS. 9A-9D showed qPCR amplification curves for detecting telomerase activity in WI-38 cell lysates of different concentrations, and in HeLa cell lysate containing one cell mixed with the WI-38 cell lysates of different concentrations. FIG. 9E showed a qPCR amplification curve for detecting telomerase activity in WI-38 cell lysate containing 8000 cells and in Hela cell lysate containing 1 cell. FIG. 9F showed a linear relationship between the Ct value and the logarithm of cell number for detecting telomerase activity in WI-38 cells. The results showed that the telomerase activity of one HeLa cell was comparable to that of 9,200 WI-38 cells. The telomerase activity in one HeLa cell was detected in the presence of WI-38 cells less than 2000. Therefore, the method for detecting telomerase activity provided by the example of the disclosure has strong anti-interference ability, and can quickly and accurately detect cancer cells from normal cells.

Example 10

Simple Method for Detecting Telomerase Activity at Single-Cell Level:

The biological samples were treated by the method in Example 6, and a flow cytometry was also prepared for use.

384-well PCR plate was pre-loaded with 1 µL of CHAPS lysate buffer in each well and placed immediately on ice. 1, 10, or 50 cells were sorted into the corresponding wells of the PCR plate using flow cytometry. The cells were lysed on ice for 20 min, followed by addition of 9-µL reaction solution containing a telomerase reaction system and a qPCR reaction system. 9-µL reaction solution containing the following compositions: 5 µL of 2×PCR mix (Plexor qPCR Systems), 0.4 µL of FAM-(iso-dC) modified primer STS (5 µM) (upstream primer), 0.4 µL of primer ACX (5 µM) (downstream primer), 0.15 µL of DMSO, 0.15 µL of 10 mg/mL BSA and 2.9 µL of ddH$_2$O.

Detection of telomerase activity was carried out using the single-step method, and the reaction conditions were the same as those of the single-step method in Example 2. The one-step reaction was performed on a QuantStudio 12K Flex real-time PCR system in which the annealing temperature in 4) was 57° C.

Figure 10A:
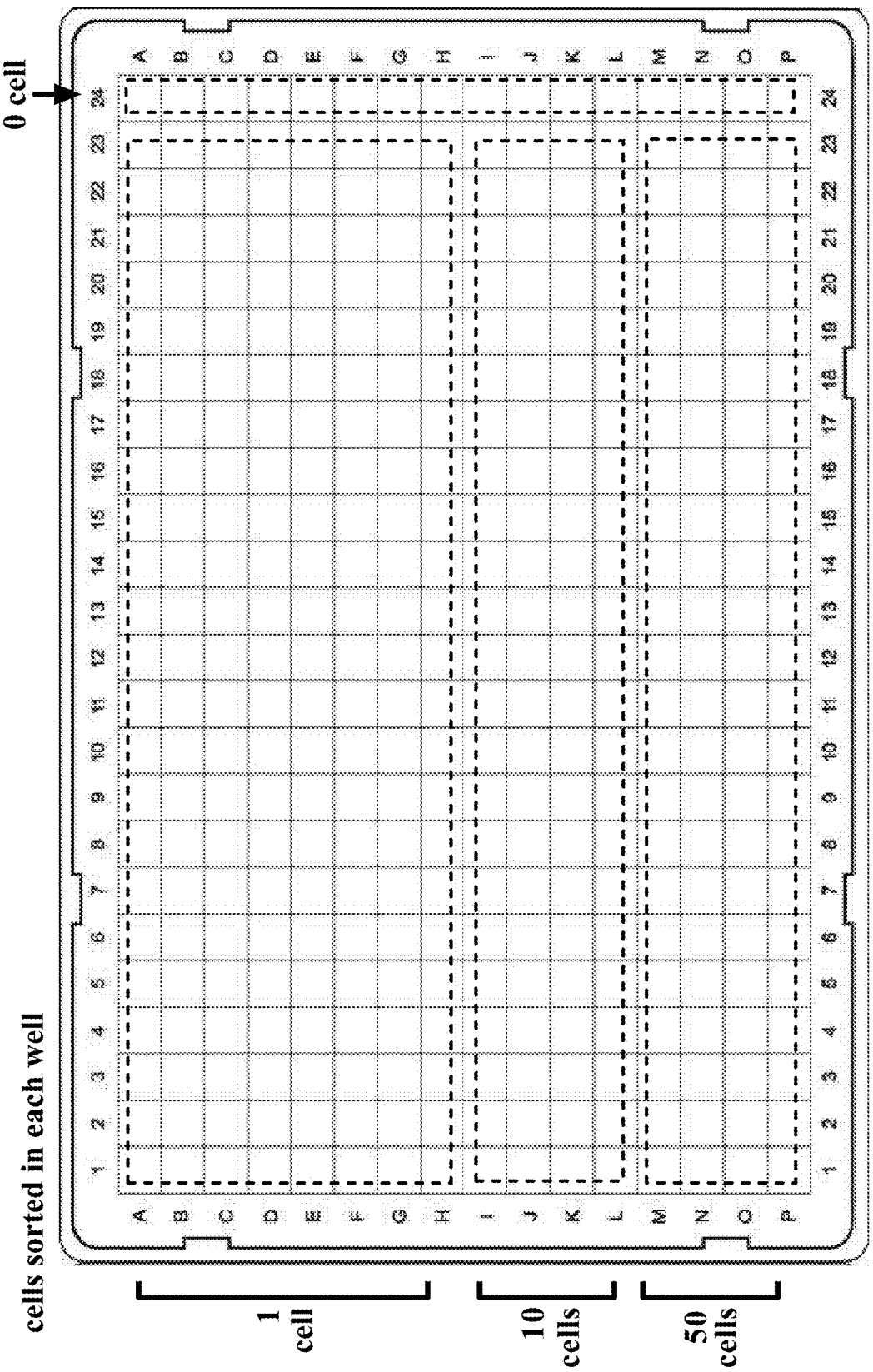
FIG. 10A shows distribution and number of samples in 384-well plates when detecting telomerase activity in 1, 10 and 50 Hela cells. FAM-(iso-dC) modified primer STS is an upstream primer, and Primer ACX is a downstream primer.
Figure 10B:
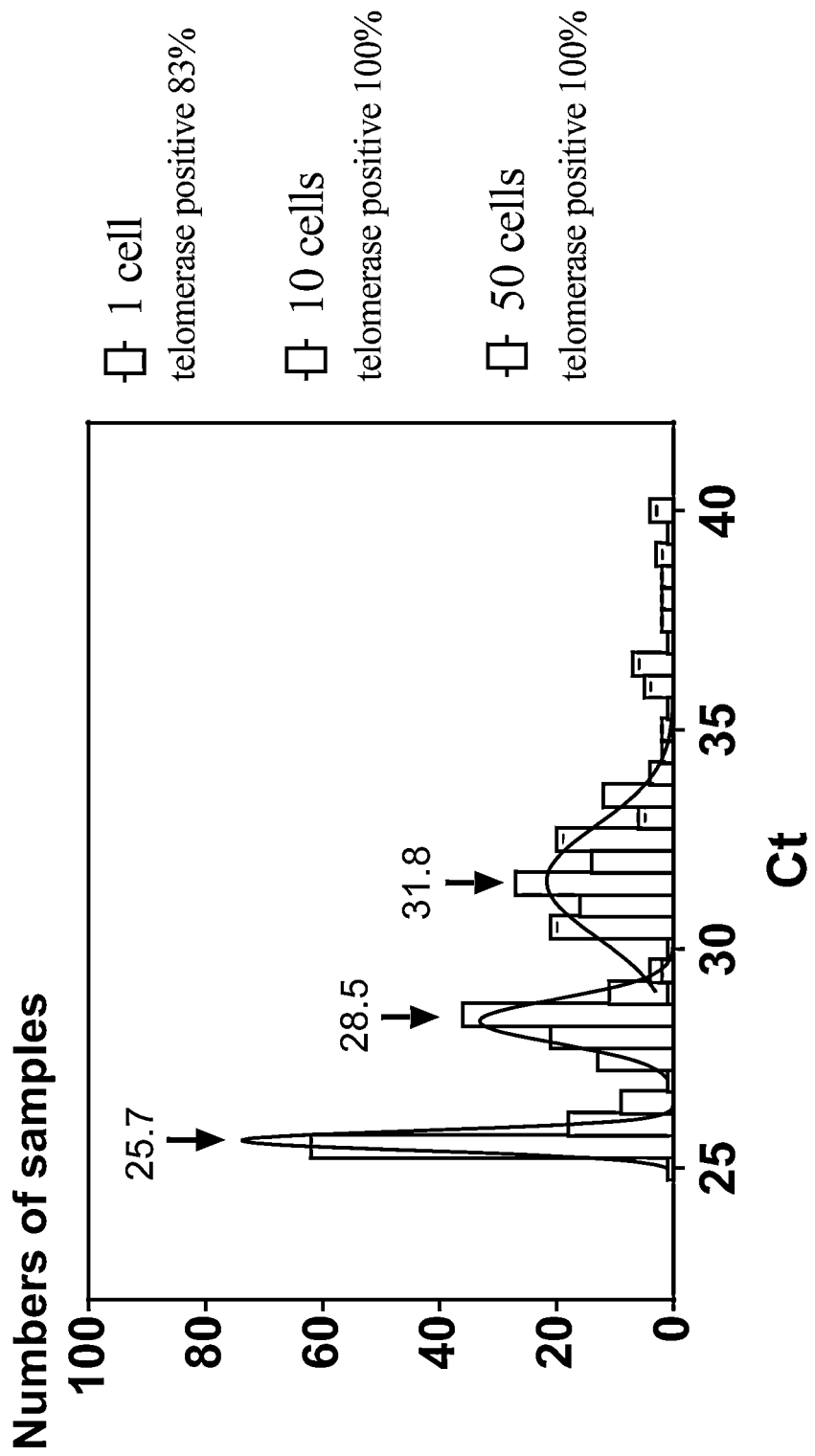
FIG. 10B shows a Ct value distribution in each group of samples detected for telomerase activity in 1, 10, and 50 Hela cells. FAM-(iso-dC) modified primer STS is an upstream primer, and primer ACX is a downstream primer.

FIG. 10A showed the distribution of reaction systems of single cell, 10-cell, and 50-cell samples in a 384-well plate. FIG. 10B gives the Ct value of single cell, 10-cell, and 50-cell samples. The fluorescence signal reduced by 10% was defined as a threshold at which the corresponding cycle number of qPCR amplification was Ct value. The results showed that the positive rate of telomerase activity in a single Hela cell was 83%, and the single Hela cell feature a wide variation in the Ct value around an average of 31.8. The positive rates of telomerase activity in the 10-cell and 50-cell were 100%, respectively. When the number of cells increased to 10 and 50, the mean Ct values dropped respectively, as expected with a much narrower variation. The average telomerase activity of the three cell samples had a strict correspondence with the number of cells.

Example 11

Detection of Telomerase Activity in TERT Over-Expressing Cell:

Hela-S3 cells were cultured in 6-well plates to a density of 70-80%. 1 µg of pCMV-TERT-IRES-EGFP plasmid expressing the TERT protein and 1 μg of control plasmid without the TERT gene were transfected with Lipofectamine 2000. After transfection for 24 h, the cells were digested with 0.5% trypsin and stopped by addition of DMEM medium containing 10% fetal bovine serum. The suspended cells were centrifuged at 500×g for 3 min followed by removal of the medium. The cell pellets were resuspended in 1 mL of PBS, and the cells carrying EGFP signals were sorted using flow cytometry (MoFlo XDP) into vials of 96-well plate each containing 2 μL of CHAPS lysate buffer. By a flow cytometry using single-cell mode, single cell or 10 cells were aspirated and transferred to the corresponding wells of the 96-well plate. The 96-well plate was then lysed on ice for 30 min.

Detection of telomerase activity was carried out by the two-step method in Example 2. 2×PCR mix was from the qPCR kit using Plexor qPCR Systems, FAM-(iso-dC) modified primer MTS was used as the upstream primer, and primer Beacon ACX62-2C was used as the downstream primer. The annealing temperature in 3) of the qPCR amplification was 60° C.

Figure 11:
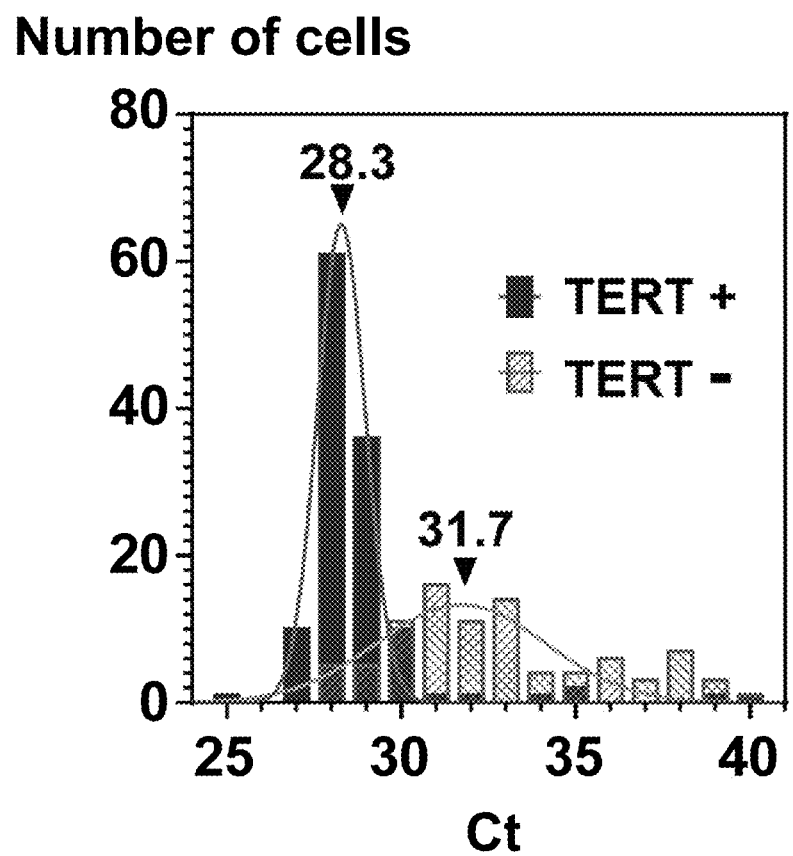
FIG. 11 shows a Ct value distribution map of quantitative PCR for detecting telomerase activity before and after overexpression of TERT protein in a single Hela-S3 cell. FAM-(iso-dC) modified primer STS is an upstream primer, primer Beacon ACX62-2C is a downstream primer.

The results of telomerase activity in Hela-S3 cells were shown in FIG. 11. In comparison with the cells transfected with a control vector, the Hela-S3 cells overexpressing TERT protein displayed at least 10 times much higher telomerase activity with a much higher proportion of telomerase-positive cells. The results indicated that the method of Example 11 can be used to detect the changes of telomerases in single cells.

Example 12

Detection of Telomerase Activity Using Upstream Primers Modified by Environmentally Sensitive Fluorescent Reporters:

The cell lysate obtained in Example 1 was diluted with CHAPS lysate buffer to obtain cell lysates equivalent of 1000, 200, 40, 8, and 1.6 Hela cells, respectively. The CHAPS lysate buffer containing 1000 cells, which was inactivated at 95° C. for 5 min, was used as a telomerase-negative control.

The telomerase activity was detected by the single-step method in Example 2. 2×PCR mix was from the qPCR kit using Gotaq probe qPCR Systems. The upstream primers were Bodipy modified primers CTS and TAMRA modified primers CTS, respectively. The downstream primers were primer ACX. The annealing temperature in 4) of the qPCR reaction was 57° C.

Figures 12A, 12B:
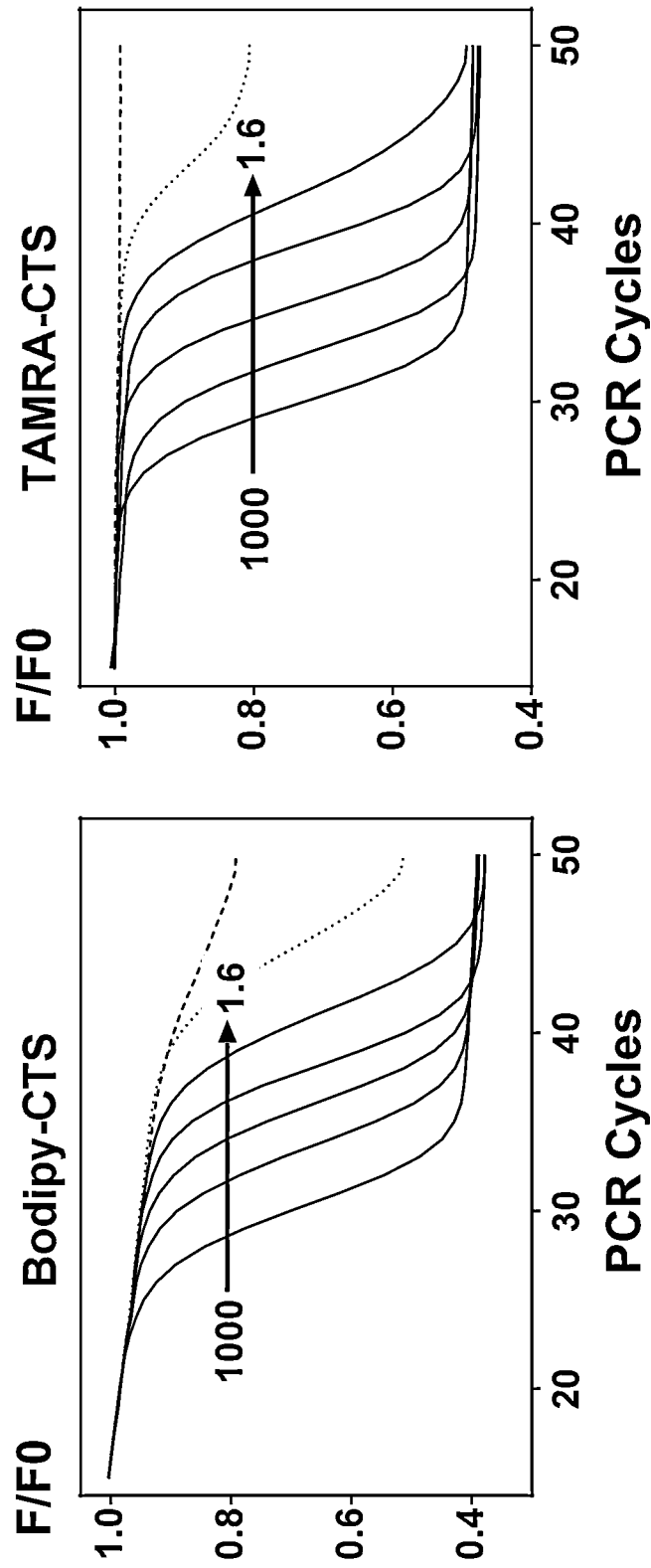
FIG. 12A shows quantitative PCR curves for detecting telomerase activity in 1000, 200, 40, 8, and 1.6 Hela cells. Bodipy modified primer CTS is an upstream primer, and Primer ACX is a downstream primer.
FIG. 12B shows a linear relationship between Ct-value and logarithm of cell number in quantitative PCR for detecting telomerase activity in 1000, 200, 40, 8, and 1.6 Hela cells. Bodipy modified Primer CTS is an upstream primer, and primer ACX is a downstream primer.
Figures 12C, 12D:
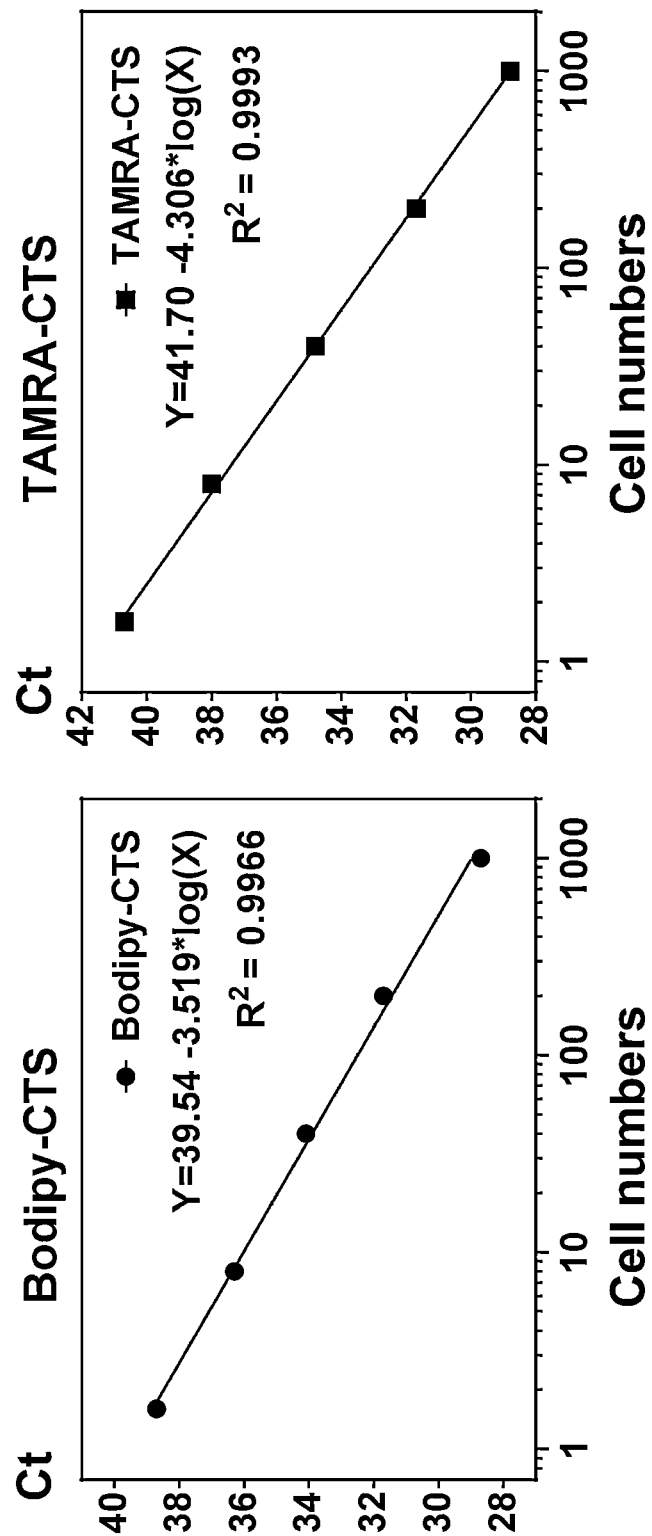
FIG. 12C shows quantitative PCR curves for detecting telomerase activity in 1000, 200, 40, 8, and 1.6 Hela cells. TAMRA modified primer CTS is an upstream primer, and primer ACX is a downstream primer.
FIG. 12D shows linear relationship between Ct value and logarithm of cell number in quantitative PCR for telomerase activity in 1000, 200, 40, 8, and 1.6 Hela cells. TAMRA modified primer CTS is an upstream primer, and primer ACX is a downstream primer.

Detection results of telomerase activity were shown in FIGS. 12A-12D. In FIGS. 12A and 12C, the abscissa represents number of PCR cycles, the ordinate represents correction value of the fluorescence signal from the sample at each cycle number, and the solid lines from left to right represents amplification curves of 1000, 200, 40, 8, 1.6 cells, respectively. The dotted line represents amplification curves of two control samples containing 1000 inactivated cells and 0 cells, respectively. In FIGS. 12B and 12D, a linear relationship between the Ct value and the logarithm of the cell number was obtained by plotting the logarithm of the cell number as the abscissa. The results showed that the Bodipy modified primer STS or TAMRA modified primer STS as upstream primer can be used to detect telomerase activity of different concentrations. The resulting amplification curve exhibited a similar shape with that obtained with the kit using plexor qPCR system. The Ct values of the samples showed a good linear relationship with the number of cells. The use of Bodipy or TAMRA modified primer CTS had a great advantage in low cost, that is, the detection for qPCR products can be performed by modification of a cheap fluorescent reporter group.

It will be obvious to those skilled in the art that changes and modifications may be made, and therefore, the aim in the appended claims is to cover all such changes and modifications.

What is claimed is:

1. A primer set for detecting telomerase activity, the primer set comprising a first primer set or a second primer set; wherein:
the first primer set comprises: an upstream primer having a sequence of SEQ ID NO: 8; and a downstream primer selected from the group consisting of having a sequence of SEQ ID NO: 4 or SEQ ID NO: 5;
the second primer set comprises: an upstream primer having a sequence of SEQ ID NO: 7; and a downstream primer having a sequence of SEQ ID NO: 2, SEQ ID NO: 3, SEQ ID NO: 4, or SEQ ID NO: 5.

2. The primer set of claim 1, wherein a 5'-end of the upstream primer of the first primer set and a 5'-end of the upstream primer of the second primer set are both labeled with a fluorescent reporter group.

3. The primer set of claim 2, wherein the fluorescent reporter group is located on an iso-dC nucleotide or a dCTP nucleotide at the 5'-end of the upstream primer.

4. The primer set of claim 2, wherein the fluorescent reporter group is selected from the group consisting of fluorescein amidite, boron-dipyrromethene, and tetramethylrhodamine.

5. The primer set of claim 3, wherein the fluorescent reporter group is selected from the group consisting of fluorescein amidite, boron-dipyrromethene, and tetramethylrhodamine.

6. A method for detecting telomerase activity of a biological sample using the primer set of claim 1, the method comprising:
1) lysing the biological sample with a 3-((3-cholamidopropyl)dimethylammonio)propanesulfonate (CHAPS) lysis buffer to obtain a cell lysate solution;
2) performing a telomerase extension in the cell lysate solution in the presence of the upstream primer of the first primer set or the second primer set of the primer set to obtain a telomerase template; and
3) conducting a qPCR amplification with the telomerase template in the presence of a corresponding downstream primer of the upstream primer of the first primer set or the second primer set used in the telomerase extension in 2).

7. The method of claim 6, wherein in 1), obtaining the cell lysate solution comprises: suspending cells of the biological sample in a phosphate buffer saline (PBS) solution, centrifuging the PBS solution comprising the cells at 500×g for 3 min, removing a supernatant of the PBS solution and repeating the centrifuging and removing the supernatant for 3 times; resuspending the cells in an isotonic buffer, dispersing the cells, adding the cells to 2 volumes of CHAPS lysis buffer with respect to a volume of the cells, lysing the cells on an ice for 30 min, centrifuging the cells at 16000×g for 20 min, collecting a supernatant and/or storing the supernatant at −80° C.

8. The method of claim 6, wherein in 1), obtaining the cell lysate solution comprises: adding 1-175 µL of the CHAPS lysis buffer to a PCR tube, aspirating single or multiple cells of the biological sample into the PCR tube by a flow cytometer or a glass tube under a microscope, and lysing the cells on an ice for 10-30 min to obtain the cell lysate solution.

9. The method of claim 6, wherein the method is implemented in a PCR tube provided with 20-µL of a reaction solution comprising 10 µL of 2×PCR mix, 0.8 µL of the upstream primer, 0.8 µL of the downstream primer, 2 µL of the cell lysate solution, and 6.4 µL of double distilled water; or the method is implemented in a PCR tube provided with 10 µL of a reaction solution comprising 5 µL of 2×PCR mix, 0.4 µL of the upstream primer, 0.4 µL of the downstream primer, 1 µL of the cell lysate solution, 0.15 µL of dimethylsulfoxide (DMSO), 0.15 µL of 10 mg/mL bovine serum albumin (BSA), and 2.9 µL of double distilled water.

10. The method of claim 9, wherein the reaction solution is treated under an extension reaction program and a PCR reaction program consecutively; the extension reaction program comprises incubation at 25° C. for 25 min, and denaturation at 94° C. for 2 min; the PCR reaction program comprises: a) denaturation at 94° C. for 30 s; b) annealing at 57-60° C. for 30 s; c) extension at 72° C. for 30 s; d. repeating operations b)-c) 45-50 times; and e) extension at 72° C. for 10 min.

11. The method of claim 6, wherein the method is implemented in a PCR tube provided with 10 µL of a first reaction system comprising 5 µL of 2×PCR mix, 0.8 µL of the upstream primer, 2 µL of the cell lysate solution, and 2.2 µL of double distilled water, and 20 µL of a second reaction system comprising 5 µL of 2×PCR mix, 0.8 µL of the downstream primers, 10 µL of telomerase template, and 4.2 µL of double distilled water; and the first reaction system and the second reaction system are added to the PCR tube in two steps.

12. The method of claim 11, wherein the PCR tube is treated under an extension reaction program and a PCR reaction program consecutively; the extension reaction program comprises incubation at 25° C. for 10-25 min, and denaturation at 94° C. for 5 min; the PCR reaction program comprises: a) denaturation at 94° C. for 2 min; b) denaturation at 94° C. for 30 s; c) annealing at 57-60° C. for 30 s; d) extension at 72° C. for 30 s; e) repeating operations b)-d) 45-50 times; and f) extension at 72° C. for 10 min.

13. The method of claim 6, wherein the CHAPS lysis buffer comprises 15 mM of Tris-HCl (pH 7.5), 2 mM of $MgCl_2$, 1.5 mM of ethylene glycol tetraacetic acid (EGTA), 0.75% of CHAPS (m/v), 15% of glycerol (v/v), 7.5 mM of dithiothreitol (DTT), 0.75 mM of a protease inhibitor 4-(2-aminoethyl)benzenesulfonyl fluoride hydrochloride (AEBSF), 1.5 U/µL of a RNase inhibitor, and 0.6 mg/mL of BSA.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Fully synthetic

<400> SEQUENCE: 1
agcatccgtc gagcagagtt                                        20

<210> SEQ ID NO 2
<211> LENGTH: 30
<212> TYPE: DNA
<213> ORGANISM: Artificial Sequence
<220> FEATURE:
<223> OTHER INFORMATION: Fully synthetic

<400> SEQUENCE: 2
gcgcggctta cccttaccct tacccctaacc                            30

<210> SEQ ID NO 3
<211> LENGTH: 25
<212> TYPE: DNA
<213> ORGANISM: Artificial Sequence

```
<220> FEATURE:
<223> OTHER INFORMATION: Fully synthetic

<400> SEQUENCE: 3
gtgcccttac ccttaccctt accct                                            25

<210> SEQ ID NO 4
<211> LENGTH: 32
<212> TYPE: DNA
<213> ORGANISM: Artificial Sequence
<220> FEATURE:
<223> OTHER INFORMATION: Fully synthetic

<400> SEQUENCE: 4
gttagggtac ccttaccctt acccttaccc ta                                    32

<210> SEQ ID NO 5
<211> LENGTH: 33
<212> TYPE: DNA
<213> ORGANISM: Artificial Sequence
<220> FEATURE:
<223> OTHER INFORMATION: Fully synthetic

<400> SEQUENCE: 5
ggttagggcc ttaccttac ccttaccta acc                                     33

<210> SEQ ID NO 6
<211> LENGTH: 35
<212> TYPE: DNA
<213> ORGANISM: Artificial Sequence
<220> FEATURE:
<223> OTHER INFORMATION: Fully synthetic

<400> SEQUENCE: 6
gggttaggcc cttaccctta cccttaccct aaccc                                 35

<210> SEQ ID NO 7
<211> LENGTH: 20
<212> TYPE: DNA
<213> ORGANISM: Artificial Sequence
<220> FEATURE:
<223> OTHER INFORMATION: Fully synthetic

<400> SEQUENCE: 7
agcatccgtc accgagagtt                                                  20

<210> SEQ ID NO 8
<211> LENGTH: 21
<212> TYPE: DNA
<213> ORGANISM: Artificial Sequence
<220> FEATURE:
<223> OTHER INFORMATION: Fully synthetic

<400> SEQUENCE: 8
caccatccgt caccgagagt t                                                21
```